US004001687B2

United States Statutory Invention Registration [19]

[11] Reg. Number: H1687

[45] Published: Oct. 7, 1997

Roe et al.

[54] GLUTEAL GROOVE BLOCKING DEVICE FOR DIAPERS

[75] Inventors: Donald Carroll Roe, West Chester; Kimberly Ann Dreier, Cincinnati, both of Ohio

[73] Assignee: The Procter & Gamble Company, Cincinnati, Ohio

[21] Appl. No.: 434,575

[22] Filed: May 4, 1995

[51] Int. Cl.[6] ..... A61F 13/52

[52] U.S. Cl. ..... 604/385.1; 604/378

[58] Field of Search ..... 604/385.1, 385.2, 604/378, 358, 386, 387

[56] References Cited

U.S. PATENT DOCUMENTS

| | | | |
|---|---|---|---|
| Re. 24,137 | 4/1956 | Jacks . | |
| 2,176,388 | 12/1939 | McLein | 604/385.1 |
| 2,331,355 | 10/1943 | Strongson . | |
| 2,964,039 | 12/1960 | Johnson, Jr. et al. . | |
| 3,183,909 | 5/1965 | Roehr . | |
| 3,211,147 | 10/1965 | Pherson et al. | 604/386 |
| 3,654,929 | 4/1972 | Nilsson et al. . | |
| 4,046,147 | 9/1977 | Berg . | |
| 4,433,972 | 2/1984 | Malfitano . | |
| 4,490,147 | 12/1984 | Pierce et al. . | |
| 4,585,448 | 4/1986 | Enloe . | |
| 4,595,392 | 6/1986 | Johnson et al. . | |
| 4,685,915 | 8/1987 | Hasse et al. . | |
| 4,758,240 | 7/1988 | Glassman | 604/386 |
| 4,804,380 | 2/1989 | Lassen et al. . | |
| 4,892,536 | 1/1990 | Desmarals et al. . | |
| 4,904,249 | 2/1990 | Miller et al. . | |
| 4,935,021 | 6/1990 | Huffman et al. | 604/385.2 |
| 5,057,096 | 10/1991 | Faglione . | |
| 5,171,236 | 12/1992 | Dreier et al. . | |
| 5,176,672 | 1/1993 | Bruemmer et al. . | |
| 5,178,139 | 1/1993 | Angelillo et al. . | |
| 5,211,641 | 5/1993 | Roos et al. . | |
| 5,306,266 | 4/1994 | Freeland . | |
| 5,324,278 | 6/1994 | Visscher et al. | 604/385.1 |
| 5,464,402 | 11/1995 | Zajaczkowski | 604/385.1 |
| 5,527,300 | 6/1996 | Sauer | 604/385.1 |
| 5,558,660 | 9/1996 | Dreier | 604/385.2 |

*Primary Examiner*—Michael J. Carone
*Assistant Examiner*—M. J. Lattig
*Attorney, Agent, or Firm*—Gerry S. Gressel; Larry L. Huston; E. Kelly Linman

[57] ABSTRACT

A diaper including a part for blocking movement of fecal material rearwardly out of the gluteal groove. The diaper comprises a core of absorbent material covered by top and back sheets, and a back area covering the gluteal groove. The diaper further comprises a blocking part in the back area, the blocking part being operable to create pressure in the gluteal groove to prevent the flow of fecal material rearwardly through the groove. The blocking part conforms to the shape of the groove, and it has compression and recovery ratios which enhance the conformity.

19 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

GLUTEAL GROOVE BLOCKING DEVICE FOR DIAPERS

FIELD AND BACKGROUND OF THE INVENTION

This invention relates to absorbent articles, and particularly to a diaper including a part constructed to prevent leakage of fecal material through a wearer's gluteal groove at the rear of the diaper. While the diaper is described herein in its use by a child, it may also be used by adults.

Diapers are, of course, well known and in common use. A disposable diaper usually includes a core of absorbent material enclosed on its outside by a liquid impervious backsheet and on its inside by a liquid pervious topsheet. Such a diaper usually also includes elastic leg cuffs around the wearer's legs and an elastic waist band around the wearer's waist. A problem often encountered during use of a conventional diaper as described above is that fecal material may leak from the rear of the diaper due to activity by the wearer or when the wearer sits down. The fecal material often moves through the gluteal groove (the open space between the buttocks), and in some instances may exit the diaper at the wearer's back. This situation is, of course, very undesirable because it usually necessitates additional cleaning of the wearer and, likely, cleaning of clothing and/or bedding.

Diapers are known in the prior art, having parts which are designed to extend along the gluteal groove. For example, the K. A. Dreier et al. U.S. Pat. No. 5,171,236 describes a "central spacer 56" which has "the advantage of reducing the amount of fecal material in the gluteal groove of the wearer". The M. A. Bruemmer et al. U.S. Pat. No. 5,176,672 describes a "cleft block 26", one function of which is "to aid in preventing fecal material from moving up the cleft of the baby's buttocks". The M. E. Freeland U.S. Pat. No. 5,306,266 also describes spacers 54 and 66 which may "plastically deform".

While the devices described in the prior art patents may function as purported in the patents, there is a continuing need for a diaper including an improved device for blocking the movement of fecal material along the gluteal groove of the wearer.

It is therefore a general object of the present invention to provide an improved diaper including a gluteal groove blocker which retards movement of fecal material along the gluteal groove and therefore reduces the area of the wearer's skin soiled by fecal material and the frequency of leakage of fecal material from the back of the diaper.

SUMMARY OF THE INVENTION

A diaper constructed in accordance with this invention comprises a core of absorbent core material, a liquid pervious topsheet and a liquid impervious backsheet, the two sheets enclosing the core and being attached together. The diaper when placed on a wearer includes a crotch area, a front area extending toward the wearer's navel, and a back area covering the wearer's buttocks and gluteal groove. The diaper further comprises a blocking part in the back area, the blocking part being constructed and located to block the gluteal groove and thereby retard the flow of fecal material rearwardly through the groove. The blocking part conforms well to the shape of the wearer's body and therefore effectively blocks the groove.

BRIEF DESCRIPTION OF THE DRAWINGS

The invention will be better understood from the following detailed description taken in conjunction with the accompanying figures of the drawings, wherein.

DETAILED DESCRIPTION OF THE INVENTION

Figure 2:
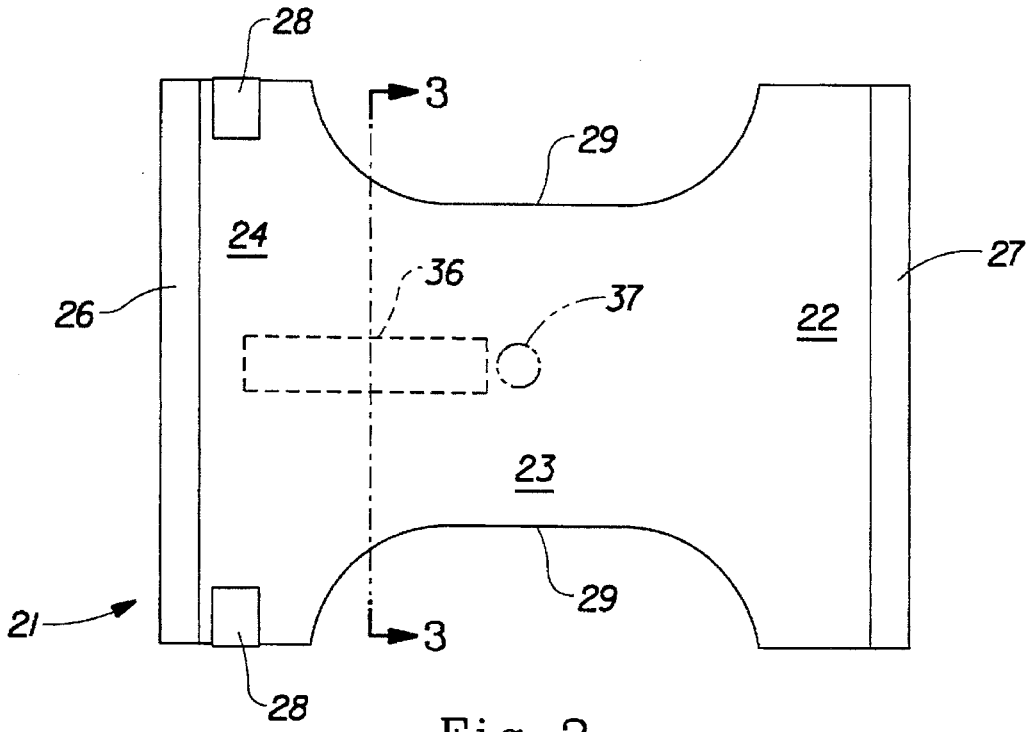
FIG. 2 is a plan view showing the diaper.
Figure 1:
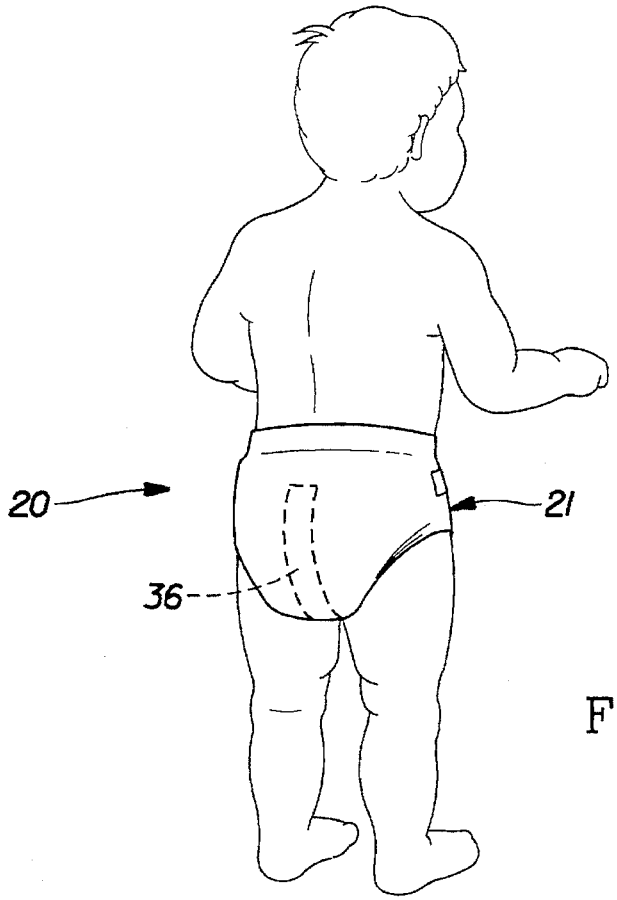
FIG. 1 is a depiction of a child wearing a diaper constructed in accordance with the invention.
Figure 3:
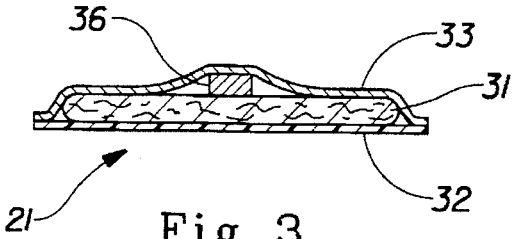
FIG. 3 is a sectional view taken on the line 3—3 of FIG. 2.

With reference first to FIGS. 1, 2 and 3, a wearer 20 (in this instance a child) is fitted with a diaper 21 which includes a front area 22 (FIG. 2), a crotch area 23 and a back area 24. When in use, the crotch area 23 extends between the legs of the wearer 20, the front area 22 extends toward the wearer's navel, and the rear area 24 extends over the wearer's buttocks and over the gluteal groove which separates the two buttocks. The rear area 24 extends past the rearward end of the groove and to the lower region of the wearer's back. The back and front borders 26 and 27 (which may be elastic) extend across the width of the diaper, and fastener tabs 28 are secured to the corners of the diaper. The tabs 28 are, of course, fastened at the waist to hold the diaper on the wearer when in use. The edges 29 of the crotch area 23 are preferably elastic. The parts of the diaper described in this paragraph may have a conventional construction.

Looking at the cross sectional view of the diaper in FIG. 3, it is formed by a core 31 of a highly absorbent core material. Across the outer side of the core 31 is a backsheet 32 of a liquid impervious material (such as plastic), and across the inner side (the skin side) of the diaper is a topsheet 33 of a soft liquid pervious material. The parts 31, 32 and 33 may be formed of conventional materials in common use for these purposes, such materials being disclosed, for example, in the K. A. Dreier U.S. Pat. No. 5,171,236. The disclosure of U.S. Pat. No. 5,171,236 is incorporated herein by reference. At the edges 29 of the diaper and at the borders 26 and 27, the sheets 32 and 33 are sealed together and enclose the core 31, the sheets 32 and 33 also being attached to the core 31.

In accordance with this invention, the diaper 21 further includes a blocking part 36 which is located in the back area 24. When worn, the blocking part 36 is located to extend from approximately the rearward side of the wearer's anus (indicated by the dotted line 37 in FIG. 2) to a location adjacent the back border 26. Further, the part 36 is located along the lengthwise centerline of the diaper, and as a consequence, it extends along the gluteal groove of the wearer. The dimensions, the shape and the compression and recovery criteria of the part 36 are such that it conforms substantially to the shape of the wearer's body and extends at least partially into the gluteal groove. By extending into the gluteal groove, the part 36 blocks or at least substantially retards the flow of fecal material rearwardly through the groove and out of the backside of the diaper.

The blocking part 36 may be located between the topsheet 33 and the core 31 as shown in FIG. 3 and press the topsheet 33 against the wearer. Instead, it may be located on the outer side of the core 31 (between the core 31 and the backsheet 31) as shown in FIG. 4 and press the topsheet 33 plus the core 31 toward the wearer.

As previously mentioned, the blocking part 36 extends along the wearer's gluteal groove and it is constructed to conform to the contour of the wearer and extend into the groove. This may be accomplished, for example, by appropriately shaping the blocking part, by forming the part with compression and recovery characteristics which produce such conformity, and/or by forming the blocking part with areas or portions having different compression and recovery characteristics.

Figure 4:
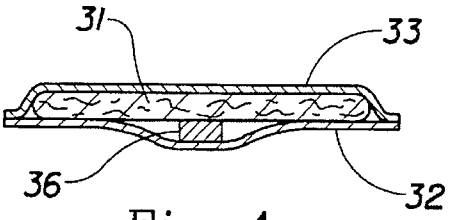
FIG. 4 is a view similar to FIG. 3 but showing an alternative construction of the diaper.
Figure 5:
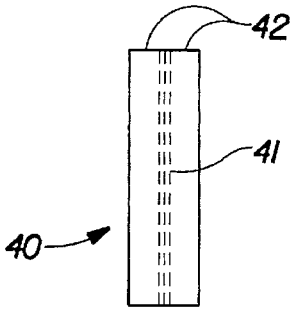
FIG. 5 is a plan view of a blocking part of the diaper shown in FIGS. 1 to 4.

In FIGS. 3 to 5, the blocking part 36 has a generally rectangular shape and has a substantially constant thickness. It is fastened, as by a moisture impervious adhesive, to one or more of the core 31, topsheet 33 (FIG. 3) and the backsheet 32 (FIG. 4). The part 36 (and the parts 40, 46 and 49 described hereafter) may be made of a compressible and resilient material such as sponge, open or closed cell foam, nonwoven highloft materials or formed scrim structures. As a specific example, a highloft material of polyester batting such as Mountain Mist #206 made by the Stearns Technical Textiles Co. of Cincinnati, Ohio may be used. This batting has an 88% compression ratio and a 94% recovery ratio. In some embodiments, combinations of the above materials with conventional absorbent materials such as airfelt or super absorbent polymers may be used.

As illustrated in FIG. 5, a part 40 is elongated in the front-to-back direction. Along the center line (in the direction of elongation) in the portion indicated by the marks 41 in FIG. 5, the part 40 may be made stiffer than along the two side portions 42. Consequently, when the part 40 is pressed against the wearer, the center portion being stiffer and less compressible, may project into the gluteal groove whereas the side portions 42 may be pressed back from the center portion 41. Thus, the part 40 substantially conforms to the shape of the wearer. The center portion 41 may be made stiffer by various means such as by applying an adhesive to it, or by making the center portion 41 more dense, for example.

Figure 6:
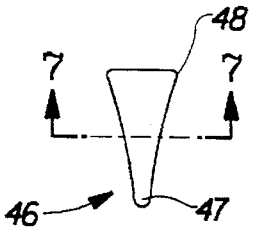
FIG. 6 is a plan view of another blocking part constructed in accordance with the invention.
Figure 7:
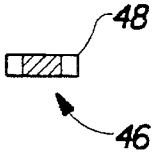
FIG. 7 is a sectional view taken on the line 7—7 of FIG. 6.

In FIGS. 6 and 7, a blocking part 46 is located similarly to the part 36 but is contoured to better fit the gluteal groove. The part 46 widens or flares laterally and toward its end which is adjacent the back border 26, thereby producing a narrow end 47 and a wide end 48. The amount of the widening is exaggerated in the drawings.

Figure 8:
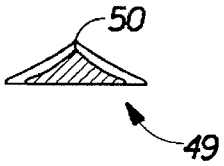
FIG. 8 is a view similar to FIG. 7 but showing an alternative form.

The blocking part 49 shown in FIG. 8 has both a flare as shown in FIGS. 6 and 7 and a peaked shape in cross section. The height of the peak 50 may also vary as illustrated in FIG. 8 (the peak 50 is preferably highest at the end which is adjacent the back border 26 but the highest point may be anywhere along the length of the blocking part).

Figure 10:
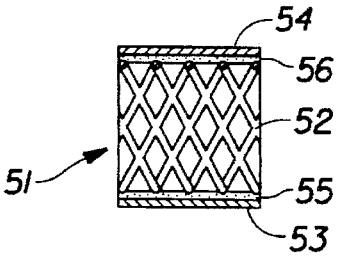
FIG. 10 is a sectional view taken on the line 10—10 of FIG. 9.
Figure 9:
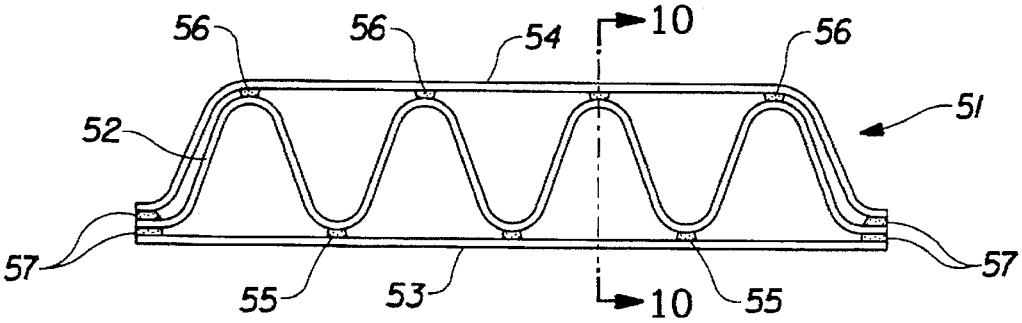
FIG. 9 is a side view showing still another alternative form of the blocking part.

FIGS. 9 and 10 show a blocking part 51 formed by a folded resilient strip 52 and two elastic strips 53 and 54. As shown in FIG. 9, the resilient strip 52 is fastened between the two strips 53 and 54. As a specific example of this embodiment, the strip 52 comprises an elongated strip of mesh or scrim of a flexible plastic and the strips 53 and 54 are made of an elastic material. In this specific example, the strip 52 is a Smith & Nephew PC52 #P100 scrim. A sheet of such a mesh scrim has about 5 relatively thicker and stiffer primary strands per centimeter (12.7 strands per inch) running in the sheet machine direction and about 10 relatively thinner and less stiff secondary strands per centimeter (25.4 strands per inch) running perpendicular to the primary strands in the sheet cross machine direction. The elastic strips 53 and 54 are ULTRAFLEX 9EX29 elastic, size 0.007"×5/64", made by Fulflex Incorporated of Middletown, R.I. To make the part 51, the strip 53 is stretched to approximately 200% of its original (relaxed) length. The scrim strip 52 is placed on the stretched strip 53 and, in this specific example, they are bonded together at approximately two inch intervals but this dimension may vary based on desired height and/or resiliency. Adhesive may be applied to bond the strips 52 and 53 at locations 55. The elastic strip 53 is then allowed to relax to its original length, and the second elastic strip 54 is bonded in a relaxed or unstressed state to the peaks of the folds of the strip 52. Adhesive may be applied to bond the strips 52 and 54 at locations 56. The ends of the three strips 52, 53 and 54 are preferably secured together at 57 as by an adhesive. Thereafter, pressure tending to move the strips 53 and 54 toward each other acts to flatten or bend the folds of the sinusoidal member 52, but the resilience of the member 52 plus the elasticity of the strips 53 and 54 cause it to tend to return to the sinusoidal shape, and it produces a resilient force or pressure in the vertical direction as seen in FIG. 9. This force or pressure is utilized to press the topsheet 33 into the wearer's gluteal groove. The strips 53 and 54 are attached to at least some of the diaper parts 31, 32 and 33. The part 51 has a 66% compression ratio and a 93% recovery ratio.

Figure 11:
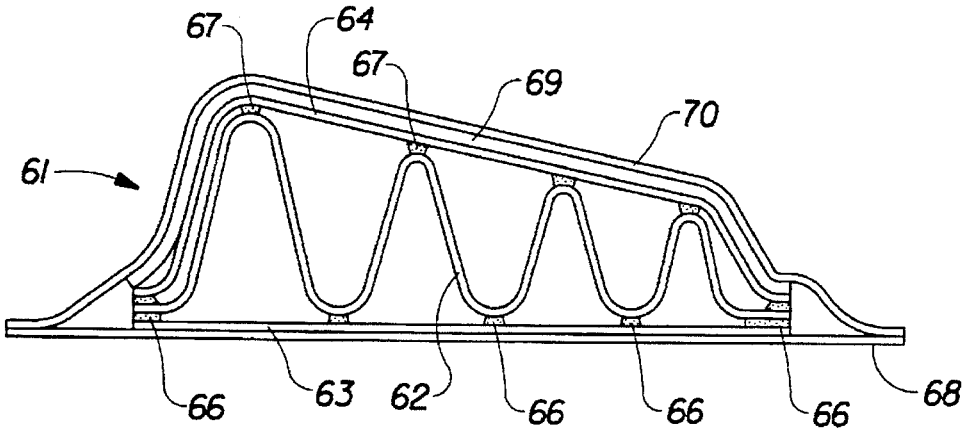
FIG. 11 is a view similar to FIG. 9 but showing another alternative form.

FIG. 11 shows a blocking part 61 which is a variation of the part 51. The part 61 includes two elastic strips 63 and 64 and a resilient strip 62 between them, the strips 62, 63 and 64 corresponding generally to the strips 52, 53 and 54. To produce an uneven spacing and height of the peaks, when assembling the parts, the left end (as seen in FIG. 11) of the elastic strip 63 is stretched to a greater degree than at the right end, and/or the spaced locations 66 where an adhesive is applied is greater than at the right end. The end result is that the peaks 67 at the left end are farther apart and higher than at the right end. In this manner, the height and stiffness of one area of the part 61 are made different from other parts. Additional layers or pads 68, 69 and 70 may optionally be applied to enclose and soften the resilient pressure applied by the strip 62.

Figure 12:
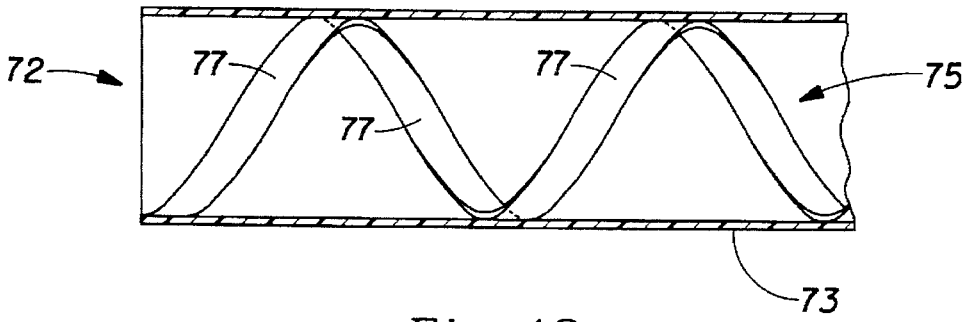
FIG. 12 is a view similar to FIGS. 9 and 11 but showing still another form of the invention.

FIG. 12 shows a blocking part 72 including a rolled or coiled strip 75 of mesh or scrim, which may be of a material similar to that of the member 52, and a cover 73. The strip 75 is rolled or coiled to form a plurality of spiral loops 77 having, as a specific example, a 15 mm diameter. The strip 75 is wrapped in a tubular glue-sprayed polypropylene nonwoven sheet 73 for stability. The sheet 73 may be product P-8 of Fiberweb Co. of Simpsonville, S.C. The glue spray may be Findley Adhesives Incorporated (Milwaukee, Wis.) #2103 adhesive.

Figure 13:
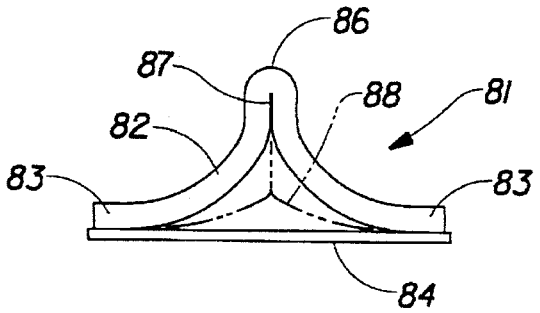
FIGS. 13 and 14 are views showing still additional forms of the invention.

In FIG. 13, a resilient blocking part 81 is provided including a thin resilient sheet 82 of a material such as polyurethane foam. As a specific example, the sheet 82 may be a polyether open cell foam #12536 from Flexible Company of Spencerville, Ohio having a density of 1 lb./ft$^3$. The sheet 82 is partially folded to form two laterally spaced feet 83 that are adhesively secured to a strip 84. The strip 84 may be formed of the same material as the sheet 82 or of a different material. The portion of the sheet 82 between the feet 64 is creased or thermally molded to form a peak 86 which, in use, extends toward the topsheet 33 and the wearer. The peak 86 is resiliently compressible and presses the topsheet 33 toward the gluteal groove of the wearer. The two undersides of the strip 82 may be glued or otherwise bonded together at 87 immediately under the peak 86 to stiffen the peak. Further, the amount or extent of the undersides which are bonded together may be varied along the length of the part 81 to vary the height and stiffness of the part. The dashed lines 88 illustrate an instance where a greater amount of the undersides is secured together, producing a lower height and stiffer portion of the part 81.

Figure 15:
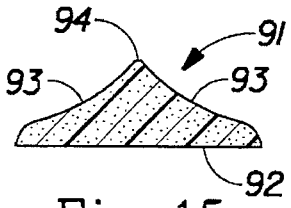
FIG. 15 is a sectional view taken on the line 15—15 of FIG. 14.
Figure 14:
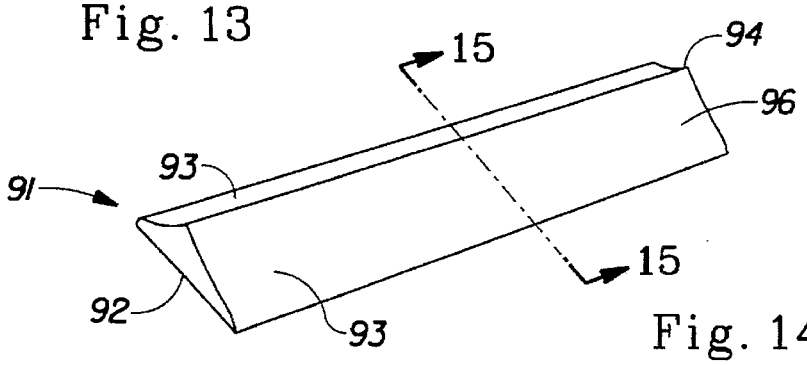

FIGS. 14 and 15 illustrate a blocking part 91 made of a resilient material such as open or closed cell plastic foam or sponge material. The part 91 has a relatively broad base 92 and sides 93 which converge to form a peak 94. As is also true of the other forms of the invention, the sides 93 and the peak 94 are shaped to conform to the gluteal groove area of the wearer. One end portion 96 (FIG. 14) of the part 91 is optionally stiffened as by applying an adhesive coating to it. The end portion 96 could instead be stiffened by other means such as by increasing its density.

In the embodiments of the invention shown in FIGS. 9 to 12, the strips 53, 54, the strips 63, 64, and the strip 73 may be attached directly to the top or back sheets 32 and 33 and/or to the core 31.

In an alternative embodiment, one or both of the strips 53, 54; 63, 64; and 73 may be omitted and the strips 52, 62 and 75 joined directly to the core and/or the top or back-sheets.

The strips 52, 62 and 75 can be formed from a number of suitable materials, including but not limited to woven or nonwoven sheet material of plastic, plastic films, and natural or synthetic rubber strands. One suitable material from which the strips 52, 62 and 75 can be formed is the above-mentioned #P100 polypropylene mesh scrim from Smith and Nephew Plastics, Ltd. of Gilberdyke, North Humberside, UK. The strips 52, 62 and 75 may comprise a 6.0 mm wide strip of the #P100 mesh cut parallel to the primary strands, so that the primary strands extend along the length of the strips and generally parallel to the gluteal groove. Another suitable material from which the strips 52, 62 and 75 can be formed comprises a polypropylene mesh scrim having a basis weight of about 50 grams per square meter (10 lbs./1000 square feet) available as ON7100 polypropylene mesh from Conwed Plastics of Minneapolis, Minn. which has squares 4 mm on each side.

The strips 53, 54, 63, 64 and 73 may be formed from a number of types of elastic material including natural or synthetic rubber strands, elastic woven or nonwoven materials, and elastic films. One suitable material from which these strips may be formed is an elastic tape sold by Fulflex, Inc. of Middletown, R.I. as ULTRAFLEX MODEL 9EX29 elastic tape. The strips 53, 54, 63, 64 can each comprise a length of an elastic tape having a width of between about 4.0 and 6.0 mm and a thickness of about 2.0 mm. Alternatively, they can each comprise a 6.0 mm wide strip of EXX-500 elastic sheet material available from the Exxon Company of Houston, Tex.

The pleats of the folded strips 52 and 62 can be formed by elastic contraction of one or both of the pairs of elastic strips 53, 54, 63 and 64 relative to the folded strips. For instance, a folded strip can have a free (unstretched) length which is greater than the free length of the elastic strips. The elastic strips can be elongated or stretched relative to their free lengths and relative to the folded strips. While elongated, the elastic strips can be attached to the folded strips at spaced apart locations along the length of the folded strips. When the forces causing the elongation of the elastic strips are released, the elastic strips will contract relative to the folded strips, thereby drawing the spaced apart attachment points on the folded strips together to form the pleats.

Percentage elongation is determined by subtracting an elongated length from the free gage length, and dividing the difference by the free gage length. For elastic strips 53 and 54, for example, formed from the ULTRAFLEX elastic tape listed above, a suitable folded member 52 with pleats can be made by providing a percentage of elongation in the elastic strips 53, 54 of between about 35 and about 400 percent. The strip 53 and/or the strip 54 can be attached to the strip 52 at locations spaced apart a distance of between about 25.4 mm (1.0 inch) and about 127 mm (5.0 inch) as measured when the elastic strips are elongated and prior to gathering of the strip 52 by contraction of the elastic strips.

In the embodiment shown in FIGS. 9 and 10, the Z-direction height (in the vertical direction as seen in FIG. 9) of the pleats is generally uniform along the length of the part 51. By way of example, this height can be between about 20 mm to about 40 mm, and the spacing between adjacent folds or pleats can be between about 25 mm to about 50 mm. For a part 51 having a strip 52 formed from the P100 mesh scrim material listed above and having elastic strips 53 and 54 formed from the ULTRAFLEX elastic tape listed above, such a uniform arrangement of the folds can be obtained where the percentage of elongation in the strips 53 and 54 is about 50 to about 400 percent and where the strips 53 and 54 are attached to the strip 52 at locations spaced apart a distance of about 25.4 mm to about 127 mm as measured when the strips 53 and 54 are elongated and prior to gathering of the strip 52 by contraction of the strips 53 and 54.

The Z-direction height of the pleats can vary along the longitudinal length as shown and described in connection with FIG. 11. Such a variation in Z-direction height can provide localized lift of the topsheet 33 for improved fit in the gluteal groove. Such a variation in Z-direction height of the pleats can be obtained by varying the percentage of elongation of the elastic strips as a function of position along the length of the folded strip prior to joining the elastic strips together.

As previously mentioned, an important feature of the invention is that the blocking part conforms well to the shape of the wearer's body, and the compression/recovery criteria of the blocking part are related to this feature. The compression factor relates to how well the blocking part conforms to the gluteal groove when the wearer sits on the part, and the recovery factor relates to how well the blocking part conforms when the wearer stands up and removes pressure on the part.

The preferred compression ratio is in the range of at least about 40%; the more preferred compression ratio is in the range of at least about 60%; and the most preferred compression ratio is in the range of at least about 80%.

The preferred recovery ratio is in the range of at least about 60%; the more preferred recovery ratio is in the range of at least about 75% and the most preferred recovery ratio is in the range of at least about 85%.

The compression and recovery ratios may be measured using an Ono-sokki Digimatic Indicator from Measure-All, Inc. of Fairfield, Ohio, using a pressure foot having a diameter of 0.95 inch. The measurements and ratios of a sample are made as follows. First, with zero pressure applied, the thickness of the sample is measured (caliper #1); then a 1.0 psi load is applied to the sample for one minute and the thickness is measured (caliper #2); and then the load is removed and immediately the thickness is measured (caliper #3). The percent compression equals (caliper #1–Caliper #2) divided by caliper #1 times 100. The percent recovery equals caliper #3 divided by caliper #1 times 100.

It will be apparent from the foregoing that a novel and useful diaper including a blocking part has been provided. The blocking part is located in the diaper and conforms to the shape of the wearer's body to block movement of fecal material along the gluteal groove.

What is claimed is:

1. A diaper for use by a wearer and comprising a pad, a topsheet and a backsheet, said pad being between and fastened to said topsheet and said backsheet, said diaper including a front area, a back area and a crotch area, said diaper being shaped to be attached to a wearer with said back area extending over the wearer's gluteal groove, and said diaper further comprising a blocking part at said back area and extending along the wearer's gluteal groove, said blocking part including a contour shaped member for extending into the wearer's gluteal groove, the contour shaped member comprising a peaked cross-section.

2. A diaper as set forth in claim 1, wherein said pad has a skin side and a back side, said blocking part being on said skin side and pressing said topsheet toward the wearer when in use.

3. A diaper as set forth in claim 1, wherein said pad has a skin side and a back side, said blocking part being on said back side and pressing said pad and said topsheet toward the wearer when in use.

4. A diaper as set forth in claim 1, wherein said contour comprises an outward flare in the direction of said back area and laterally of said back area.

5. A diaper as set forth in claim 1, wherein said means for conforming comprises a preferred compression ratio in the range of at least about 40% and a preferred recovery ratio in the range of at least about 60%.

6. A diaper as set forth in claim 5, wherein said means for conforming comprises a more preferred compression ratio in the range of at least about 60% and has a more preferred recovery ratio in the range of at least about 75%.

7. A diaper as set forth in claim 5, wherein said means for conforming comprises a most preferred compression ratio in the range of at least about 80% and a most preferred compression ratio in the range of at least about 85%.

8. A diaper for use by a wearer and comprising a pad, a topsheet and a backsheet, said pad being between and fastened to said topsheet and said backsheet, said diaper including a front area, a back area and a crotch area, said diaper being shaped to be attached to a wearer with said back area extending over the wearer's gluteal groove, and said diaper further comprising a blocking part at said back area and extending along the wearer's gluteal groove, said blocking part including blocking means for conforming to the shape of and blocking the wearer's gluteal groove when in use, the blocking means comprising a resilient folded strip including a plurality of pleats, each of said pleats including a high point and a low point, and each of said pleats being compressible to move said high point toward said low point.

9. A diaper as set forth in claim 8, wherein said blocking part further includes an elastic strip bonded to said high points of said pleats.

10. A diaper as set forth in claim 9, wherein said blocking part further includes an elastic strip bonded to said low points of said pleats.

11. A diaper as set fort in claim 8, wherein said blocking part further includes an elastic strip bonded to said low points of said pleats.

12. A diaper as set forth in claim 8, wherein said plurality of pleats have substantially the same height and length.

13. A diaper as set forth in claim 8, wherein said plurality of pleats have different heights and lengths.

14. A diaper for use by a wearer and comprising a pad, a topsheet and a backsheet, said pad being between and fastened to said topsheet and said backsheet, said diaper including a front area, a back area and a crotch area, said diaper being shaped to be attached to a wearer with said back area extending over the wearer's gluteal groove, and said diaper further comprising a blocking part at said back area and extending along the wearer's gluteal groove, said blocking part including blocking means for conforming to the shape of and blocking the wearer's gluteal groove when in use, the blocking means comprising a resilient strip rolled in a spiral form.

15. A diaper as set forth in claim 14, wherein said blocking part further comprises a cover which encloses and is bonded to said resilient strip.

16. A diaper for use by a wearer and comprising a pad, a topsheet and a backsheet, said pad being between and fastened to said topsheet and said backsheet, said diaper including a front area, a back area and a crotch area, said diaper being shaped to be attached to a wearer with said back area extending over the wearer's gluteal groove, and said diaper further comprising a blocking part at said back area and extending along the wearer's gluteal groove, said blocking part including blocking means for conforming to the shape of and blocking the wearer's gluteal groove when in use, the blocking means comprising a relatively narrow elongated member, a portion of said member having a lower compression ratio than the remainder thereof.

17. A diaper as set forth in claim 16, wherein said portion includes a stiffening material thereon.

18. A diaper for use by a wearer and comprising a pad, a topsheet and a backsheet, said pad being between and fastened to said topsheet and said backsheet, said diaper including a front area, a back area and a crotch area, said diaper being shaped to be attached to a wearer with said back area extending over the wearer's gluteal groove, and said diaper further comprising a blocking part at said back area and extending along the wearer's gluteal groove, said blocking part including blocking means for conforming to the shape of and blocking the wearer's gluteal groove when in use, the blocking means comprising an elongated strip of resilient material, said strip having a center line in the direction of elongation, and said strip being creased along said center line.

19. A diaper as set forth in claim 18, wherein said strip further includes side portions on opposite sides of said center line, and said part further includes a strip bonded to said side portions.

* * * * *